United States Patent

Shraiber et al.

[11] 4,080,839
[45] Mar. 28, 1978

[54] TESTING METHOD USING ULTRASONIC ENERGY

[76] Inventors: David Solomonovich Shraiber, Leninsky prospekt, 39, kv. 100; Boris Glebovich Golodaev, 9 ulitsa Sokolinoi gory, 3, kv. 253, both of Moscow; Leonid Mikhailovich Zakharov, Sovetsky prospekt, 14, kv. 31, Ivanteevka, Moskovskoi oblasti; Anatoly Fedorovich Razumovsky, Kantemirovskaya ulitsa, 5, korpus 1, kv. 31, Moscow, all of U.S.S.R.

[21] Appl. No.: 716,686

[22] Filed: Aug. 23, 1976

Related U.S. Application Data

[63] Continuation of Ser. No. 389,554, Aug. 20, 1973, abandoned.

[51] Int. Cl.² .................................................. G01N 29/04
[52] U.S. Cl. .................................. 73/617; 73/627; 73/642
[58] Field of Search .................................... 73/67.7

[56] References Cited

U.S. PATENT DOCUMENTS 3,325,781   6/1967   Harris .................. 73/67.7 X

*Primary Examiner*—James J. Gill
*Attorney, Agent, or Firm*—J. Harold Nissen

[57] ABSTRACT

A convergent ultrasonic beam is formed by an emitter made as a sphere and directed to a piece under test. Having been reflected from the surface of the piece and from the defect, the ultrasonic beams are separated in space. The ultrasonic beam carrying information on the defect is displayed.

9 Claims, 1 Drawing Figure

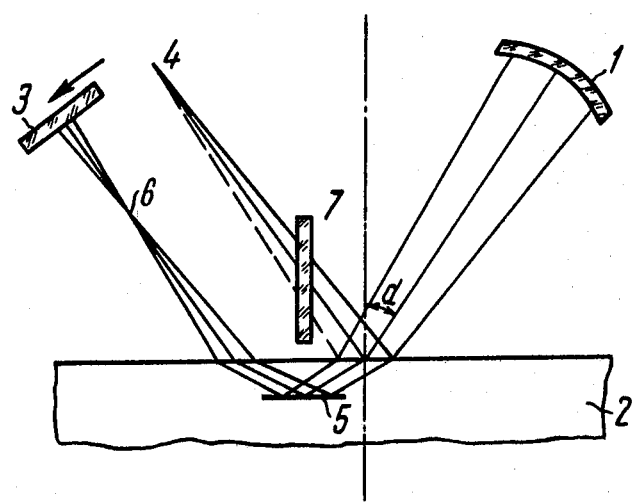

TESTING METHOD USING ULTRASONIC ENERGY

This is a continuation, of application Ser. No. 389,554 filed Aug. 20, 1973, now abandoned.

The present invention relates to improvements in the techniques of flaw detection, and more particularly to a method of ultrasonic echo flaw detection. The method of the invention may be employed, inter alia, for flaw detection in various blanks from which items for critical applications are manufactured.

Widely known in the art of ultrasonic echo flaw detection is a method, whereby an ultrasonic beam is directed through an intermediate contact (immersion) medium to a piece under test transversely to the surface thereof. Then, the ultrasonic impulses reflected from the outer surface and inner layers of the piece are received and converted to electric pluses which carry information as to the presence of defects in the piece. In this arrangement, the transducer of the tracing head of the ultrasonic echo flaw detector serves both to convert electric oscillations to acoustic and vice versa, thereby combining the functions of an ultrasonic emitter and a receiver (combined tracer). Obviously, with such a method of detection, the transducer cannot receive reflected impulses until after the emission of an ultrasonic impulse has been completed. This limits the ability to receive echo signals reflected from defects located near the surface of the piece so that there appears a "dead" zone which does not lend itself to inspection, thereby detracting from the reliability of flaw detection.

According to another known method of flaw detection, the functions of an emitter and a receiver in the transducer are divided by making the transducer composed of two piezoelectric elements (divided-combined tracer). The ultrasonic waves from the piezoelectric emitter are sent out as a divergent beam inclined at an angle relative to the normal to the surface of the piece under test, and the reflected waves are received by the piezoelectric receiver. The latter receives both the signal reflected from the surface of the piece under test and that reflected from the defect. In order that an echo signal from the defect may be discriminated, for example on an indicator screen, that echo signal must be received by the piezoelectric receiver after the echo signal reflected from the surface of the piece has been received.

Both echo signals are separated in time above all by virtue of the difference in the length of the paths they have to traverse to reach the receiver. Naturally, the path of the echo signal from the surface of the piece is always shorter than that of the signal reflected from the defect. It follows that the echo signal reflected from the defect will arrive with a certain delay relative to the echo signal reflected from the contact surface.

But in order that the two echo signals may be separated on the indicator screen, it is necessary that the echo signal from the defect should arrive after the echo signal from the contact surface is over or, to be more precise, after the amplitude of the latter signal has diminished to a certain predetermined minimum. Obviously, for the signals reflected from the contact surface and from the defect to be displayed separately, it is required, apart from increasing the difference in the paths traversed by the signals, also to decrease the duration of the echo signal reflected from the contact surface. As the depth at which the defect lies decreases, so does the difference in the path lengths of the two echo signals, which difference ultimately tends to zero. Hence, to minimize the dead zone, the duration of the echo signal from the contact surface has to be reduced to a minimum. This duration depends on the length of the electric pulse driving the emitter and also on the Q-factor of the emitter, so that the shorter the driving pulse and the lower the Q-factor, the shorter the echo signal from the contact surface.

However, short pulses employed to drive the emitter adversely affect the sensitivity of the detector, since the resonance properties of a piezoelectric element cannot be utilized however high its Q-factor may be, for the pulse is over long before the oscillation of the piezoelectric element reach their maximum amplitude. Therefore, this method of decreasing the dead zone is ineffective, for at a required level of sensitivity the dead zone persists and reaches 15 to 20 mm in length, resulting in the need for an additional allowance in the blank which allowance is subsequently lost in pieces.

It is an object of the present invention to provide an improved method of ultrasonic echo flaw detection, such as will reduce the length of the minimized dead zone by preventing the interfering echo signal from the contact surface from reaching the piezoelectric receiver and would also permit minimizing the amount of waste metal.

This and other objects are attained in a method of ultrasonic echo flaw detection which consists in directing ultrasonic waves through an immersion medium to a piece under test at an angle relative to the normal to the surface thereof and receiving the reflected waves carrying information as to the presence of a defect, whereby, in accordance with the invention, the ultrasonic waves are emitted as a convergent beam which, having been reflected, is focused in the vicinity of the plane wherein the piezoelectric receiver is disposed.

The proposed method of ultrasonic echo flaw detection ensures distinct space separation of the beams and permits of utilizing driving pulses of a greater duration. These features improve the sensitivity and resolving power of a flaw detector in detecting small-size defects occurring at a small depth in the piece under test.

The waves reflected from the surface of the piece are to be screened off.

The piezoelectric emitter is preferably formed as part of a spherical surface.

An embodiment of the present invention will now be described, by way of example, with reference to the accompanying drawing which shows the arrangement of the emitter and the receiver as well as the paths of the beams.

An emitter 1 generating ultrasonic waves is formed as part of a sphere, whereof the radius is equal to the sum of the distances (along the path of the ultrasonic beam) from the centre of the surface of the emitter 1 to the point of incidence of the ultrasonic beam on the surface of a tested piece 2 and from the latter point to the plane wherein a receiver 3 of ultrasonic waves is disposed. Thus, the ultrasonic emitter 1 sends out ultrasonic waves in the form of a convergent beam which, having been reflected, is focused together in the reception plane. Said ultrasonic beam is directed so that its axis is inclined at an angle $\alpha$ to the normal to the surface of the tested piece. The ultrasonic beams reflected from the surface of the piece 2 are focused at a point 4, whereas the beams refracted in the body of the piece 2 and reflected from a defect 5 are focused at a point 6. Thus, in the reception plane the waves carrying information as to the presence of a defect are found to be separated in space relative to the waves reflected from the surface of the piece 2. When displacing the ultrasonic wave receiver 3, a position is found wherein the signal reflected from the surface of the piece 2 does not reach the receiver 3.

In order that the signal reflected from the surface of the piece 2 should not reach the receiver 3, an acoustically opaque screen 7 may be additionally positioned across the path of the beam reflected from the surface of the piece 2. This provides for an additional time separation of the echo signals by increasing the angle of incidence so as to excite time-separated ultrasonic waves in the material of the piece under test.

The method of this invention substantially enhances the measurement accuracy and permits of reducing the dead zone to 2-8 mm.

What we claim is:

1. A method of testing a workpiece to detect flaws therein, comprising the steps of:

generating ultrasonic waves and emitting them as a convergent beam;

directing said emitted convergent beam as an incident beam onto the workpiece to be tested, said incident beam being directed towards the surface of the workpiece along a direction angularly displaced from the normal to the surface of the workpiece to provide waves reflected from the surface of the workpiece and waves reflected from flaws in the workpiece, waves of said incident beam entering said workpiece being refracted by the workpiece material and reflected from the flaws, and waves of said incident beam being reflected from the surface of the workpiece, said flaw reflected waves being spatially displaced from and time delayed from said surface reflected waves;

converting said flaw reflected waves into a reflected convergent beam carrying information about the flaws in the workpiece;

receiving the waves of the information carrying beam in a receiving element lying in a plane normal to the information carrying beam and containing the focal point of a convergent beam of waves reflected from the surface of the workpiece, and concentrating the waves of the surface reflected convergent beam at a focusing point spaced from the plane of the receiving element.

2. The method as set forth in claim 1, including the step of:

positioning an acoustically opaque screen across the path of the convergent beam of waves reflected from the surface of the workpiece.

3. The method as set forth in claim 2, wherein the screen is placed in the path of the surface reflected beam between the focal point thereof and the surface of the workpiece.

4. The method as set forth in claim 1, including the step of:

increasing the time delay and space separation between the surface reflected convergent beam and the flaw reflected convergent beam by increasing the angular displacement of the incident convergent beam from the normal to the workpiece surface.

5. The method as set forth in claim 4, wherein the incident convergent beam is emitted from an emitter having a surface formed from part of a sphere.

6. The method as set forth in claim 5, including the step of:

screening off the surface reflected convergent beam from the flaw reflected convergent beam.

7. The method as set forth in claim 5, including the step of:

screening off the surface reflected convergent beam prior to reaching the focal point thereof.

8. The method as set forth in claim 1, wherein said incident beam is directed through an immersion medium.

9. The method as set forth in claim 8, wherein said immersion medium is a liquid.

* * * * *